US008418695B1

(12) United States Patent
Moulton

(10) Patent No.: US 8,418,695 B1
(45) Date of Patent: Apr. 16, 2013

(54) EYEGLASS PATCH

(76) Inventor: Thomas C. Moulton, Citrus Heights, CA (US)

(*) Notice: Subject to any disclaimer, the term of this patent is extended or adjusted under 35 U.S.C. 154(b) by 38 days.

(21) Appl. No.: 13/178,209

(22) Filed: Jul. 7, 2011

(51) Int. Cl.
*A61F 9/00* (2006.01)

(52) U.S. Cl.
USPC .............................. 128/858; 2/13

(58) Field of Classification Search ......... 128/858; 2/12–13, 15
See application file for complete search history.

(56) References Cited

U.S. PATENT DOCUMENTS

| 1,310,077 | A | * | 7/1919 | Heaford | 351/47 |
| 2,172,573 | A | * | 9/1939 | Blumenthal | 2/13 |
| 4,582,401 | A | * | 4/1986 | Grindle | 351/45 |
| 5,050,982 | A | * | 9/1991 | Meissner | 351/203 |
| 5,402,189 | A | | 3/1995 | Gill | |
| 5,927,279 | A | | 7/1999 | Oviatt | |
| D432,658 | S | * | 10/2000 | Haynes | D24/208 |
| 6,193,740 | B1 | * | 2/2001 | Rodriguez | 606/204.25 |
| 6,557,995 | B1 | * | 5/2003 | Edwards | 351/47 |
| 6,582,073 | B1 | | 6/2003 | Hayes et al. | |
| 7,318,440 | B1 | | 1/2008 | Grijalva | |

FOREIGN PATENT DOCUMENTS

| CA | 2179831 | | 12/1997 |
| CN | 2610880 | Y | 4/2004 |
| JP | 2005345868 | A | 12/2005 |
| WO | WO 2009/015489 | A1 | 5/2009 |

* cited by examiner

*Primary Examiner* — Patricia Bianco
*Assistant Examiner* — Camtu Nguyen
(74) *Attorney, Agent, or Firm* — John P. Costello; Costello Law Corp.

(57) ABSTRACT

An eyeglass patch which is comprised of an optical occluding cup for correcting dominant eye vision problems is disclosed. One embodiment of the inventive eyeglass patch has an interchangeable exterior portion, wherein the wearer can interchange the exterior appearance of the eyeglass patch, at will. This embodiment is comprised of two cutouts, which thread and interlock together, wherein one of the cutouts has a decorative exterior.

4 Claims, 7 Drawing Sheets

EYEGLASS PATCH

1. TECHNICAL FIELD

This invention relates to eye patches which are used to treat eye problems relating to a dominant eye, and more specifically, this invention relates to an eyeglass patch which attaches to eyeglasses in order to block lines of sight to the dominant eye.

2. BACKGROUND

Every sighted person has one eye that is dominant to a greater or lesser degree. However, when a first eye is overwhelmingly dominant over the second, lesser eye, problems can result such as a loss of sight in the weaker eye, crossed-eyes, diverging eyes or eye muscle imbalances. In young children, if one eye shows an overwhelming dominance, an eyeglass patch is placed over the dominant eye. This treatment forces the child to rely on the weaker eye, which results in the strengthening of the weaker eye over time. In cases where the dominant eye is overwhelming, all lines of sight to the dominant eye must be blocked, including peripheral vision, in order for the weaker eye to begin to be used and to gain strength.

Additionally, for a small child, wearing an eyeglass patch can be a traumatic experience. The child may face ridicule from peers or be treated as "different" by the public at large. These negative experiences may cause the child to remove the eyeglass patch or else refuse to put one on. Therefore, any feature which makes the wearing of a corrective eyeglass patch more desirable to a child can make the difference between the treatment of a dominant eye condition, or not.

The emergence of corrective eyeglass patches having decorative features have enhanced the desirability of wearing such a patch. Examples of these type of patches center around a theme wherein the patch is designed to block all lines of sight to the dominant eye and where the patch has decorative fabric permanently sewn to the front eyeglass lens-covering portion of the device. The device is held to the glasses by sliding the temple of the glasses between the decorative fabric and an underlying colored fabric portion. The patch of JP 2005345868 shows an eye patch comprised of an eye cup with a sewn-on decorative face. A similar sewn together decorative option is represented by Patch Pals of Hiawatha, Iowa. The corrective eyeglass patch disclosed in U.S. Pat. No. 5,927,279 issued to Oviatt, incorporates fabric having a permanent decorative design.

The sewn versions of decorative eye patches are labor-intensive to make, thus reducing the profit potential for businesses that make them. Also, as noted previously, any feature which makes the wearing of a corrective eyeglass patch more desirable will cause the wearers, who are primarily children, to keep their patches in place. The decorative eyeglass patches just described, aid in this goal of achieving more desirability to the wearer. However, wearing the same sewn-on decorative design can become tiresome for the wearer, perhaps causing the wearer to fall back into the bad habit of removing the patch when not being supervised by adults.

Therefore, a need exists for a decorative corrective eyeglass patch which allows the wearer to interchange different designs upon an eyeglass patch, thus avoiding the problem of the wearer having to don the same tiresome design day after day. Also, a need exists for an alternative method to sewing the patch together which is less labor intensive.

The foregoing reflects the state of the art of which the inventor is aware, and is tendered with a view toward discharging the inventor's acknowledged duty of candor, which may be pertinent to the patentability of the present invention. It is respectfully stipulated, however, that the foregoing discussion does not teach or render obvious, singly or when considered in combination, the inventor's claimed invention.

SUMMARY OF THE INVENTION

The inventive corrective eyeglass patch allows a decorative exterior layer to be interchanged by the wearer. In this fashion, the wearer could conceivably wear an unlimited number of decorative exterior layer designs, thereby making the wearing of an eyeglass patch an exciting and creative experience. The present invention in essence converts the wearing of a corrective eyeglass patch into a fashion statement. This invention also allows a child to participate in the creation of his own eyeglass patch.

The invention is comprised of first and second cutouts made of a flexible material having strong non-fraying characteristics. The two cutouts thread together in an interlocking arrangement to form the assembly that comprises the inventive corrective eyeglass patch. In the preferred embodiment, the first cutout is a utilitarian eyeglass patch having a front portion and a side portion. The front portion blocks frontal vision and the side portion blocks the wearer's peripheral vision. The first cutout further comprises a plurality of through slits, or holes, which receive the second cutout in a threading and interlocking fashion. The second cutout has a decorative exterior surface and is comprised of an overlying member that is flanked by two threadable members. The threadable members thread through the slits present in the first cutout, and interlock with the first cutout. When fully threaded and interlocked, the overlying member of the second cutout is positioned over the front portion of the first cutout, wherein a through-channel is formed between the overlying member and front portion. The temple of a pair of eyeglasses is introduced to the through-channel with forward force, until the invention reaches the lens, wherein it is fitted over the lens of the eyeglasses. When in position, the lens is positioned in the through-channel between the overlying member and the front portion. The side portion, which bears the interlocked, decorative, threadable members, is positioned along the temple of the glasses, thereby effectively blocking the wearer's peripheral vision.

When the wearer desires to change the decorative appearance of the invention, he merely disengages the threadable members of the second cutout, from the first cutout, and threads them through the slits until they are fully disengaged from the first cutout. He then selects a second cutout having a different decorative exterior surface and re-threads and interlocks it to the first cutout.

Accordingly, the following objects and advantages of the invention apply:

It is an object of this invention to provide a corrective eyeglass patch having an interchangeable decorative component.

It is another object of this invention to provide a decorative corrective eyeglass patch which makes a fashion statement, thereby encouraging the wearer to voluntarily wear the inventive eyeglass patch.

It is another object of this invention to provide a decorative eyeglass patch for dominant eye conditions as well as any other reason that a medical professional would recommend an eyeglass patch.

A still further object of this invention is to allow a child to participate in the creation of his own decorative eyeglass patch.

It is another object of this invention to produce an eyeglass patch with an effective optical occluding cup from easily manufactured die cut shaped pieces which can be easily assembled by the consumer, thereby eliminating time intensive sewing as a method of assembling the invention.

Further objects and advantages of the invention will be brought out in the following portions of the specification, wherein the detailed description is for the purpose of fully disclosing preferred embodiments of the invention, without placing limitations thereon.

BRIEF DESCRIPTION OF THE DRAWINGS

The invention will be more fully understood by reference to the following drawings which are for illustrative purposes only.

DETAILED DESCRIPTION OF THE PREFERRED EMBODIMENTS

Figure 1:
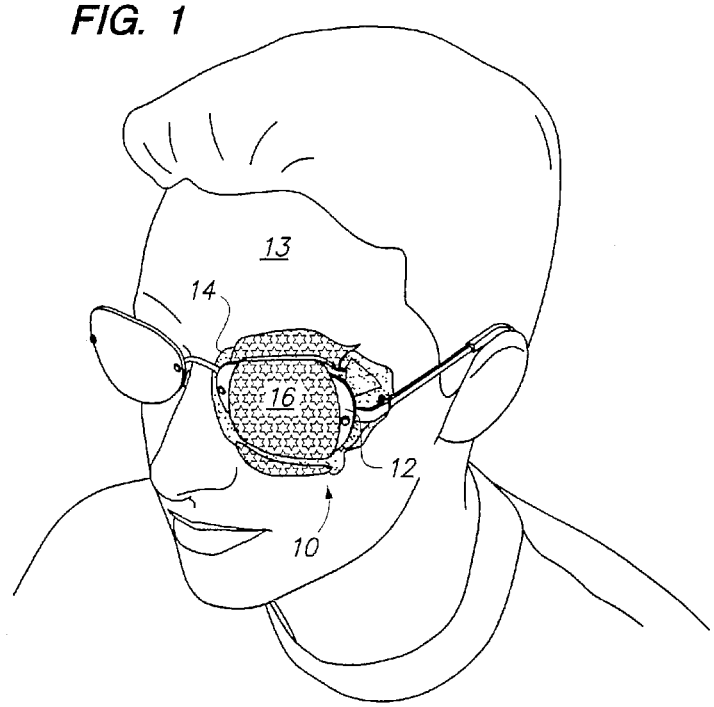
FIG. 1 is perspective view of the inventive corrective eyeglass patch, shown mounted upon the eyeglasses of a wearer
Figure 2:
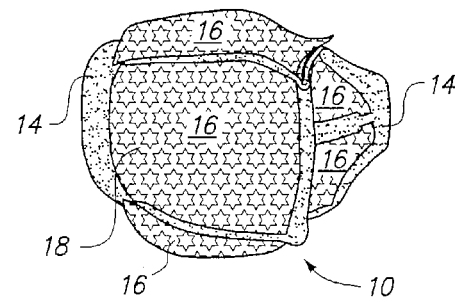
FIG. 2 is a perspective view of the inventive corrective eyeglass patch.

Referring to FIG. 1, the preferred embodiment of the inventive corrective eyeglass patch 10 mounted upon the eyeglasses 12 of a wearer 13 is shown. FIG. 2 illustrates the inventive eyeglass patch 10 by itself, which when assembled, comprises an optical occluding cup around the wearer's dominant eye, which more effectively occludes the dominant eye.

The components of this invention are die cut and not sewn together, which saves considerable assembly labor. The inventive eyeglass patch is comprised of a first cutout 14 and a second cutout 16. The second cutout 16 has a decorative exterior-facing side 18, thereby lending a fashion element to an otherwise utilitarian eyeglass patch. The second cutout 16 cooperates with the first cutout 14 by threading through slits 28, 30 (see FIG. 3) imparted through the first cutout 14, and the second cutout 16 further interlocks with the first cutout 14 to form the optical occluding cup that is the inventive corrective eyeglass patch 10. Depending on the tastes of the wearer, the second cutout 16 can be changed out, at will, and replaced with a new second cutout 16 having an entirely different exterior design. In this way, the wearer could regularly make a new fashion statement by continually replacing the second cutout 16.

Figure 3:
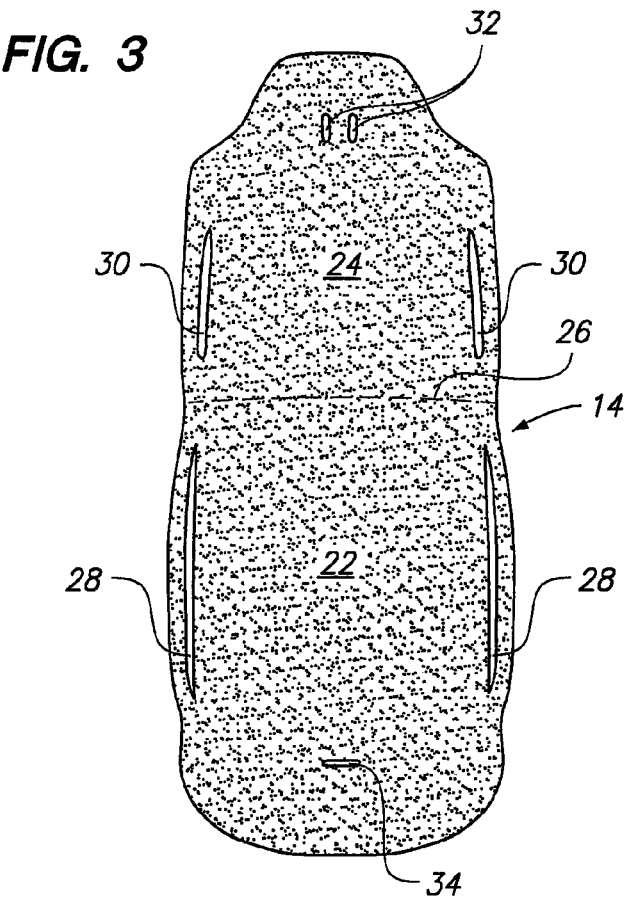
FIG. 3 is a plan view of the first cutout of the inventive eyeglass patch.
Figure 4:
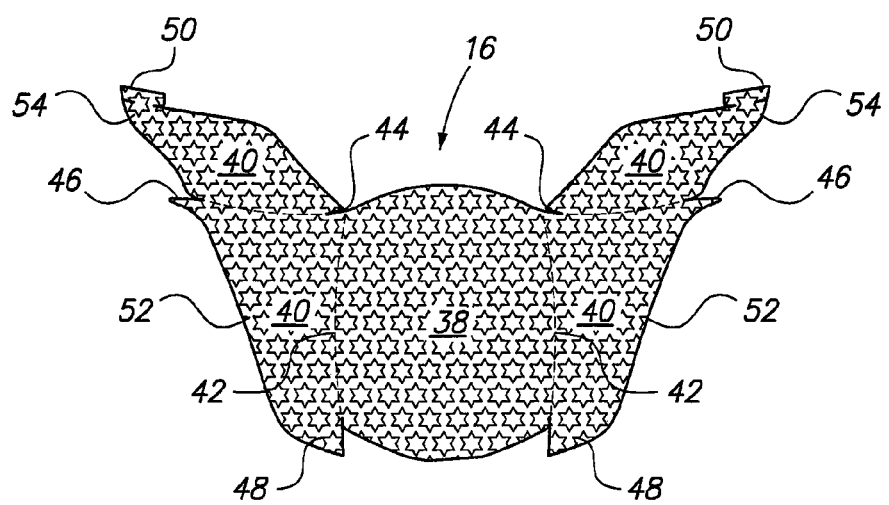
FIG. 4 is a plan view of second cutout of the inventive eyeglass patch.
Figure 5:
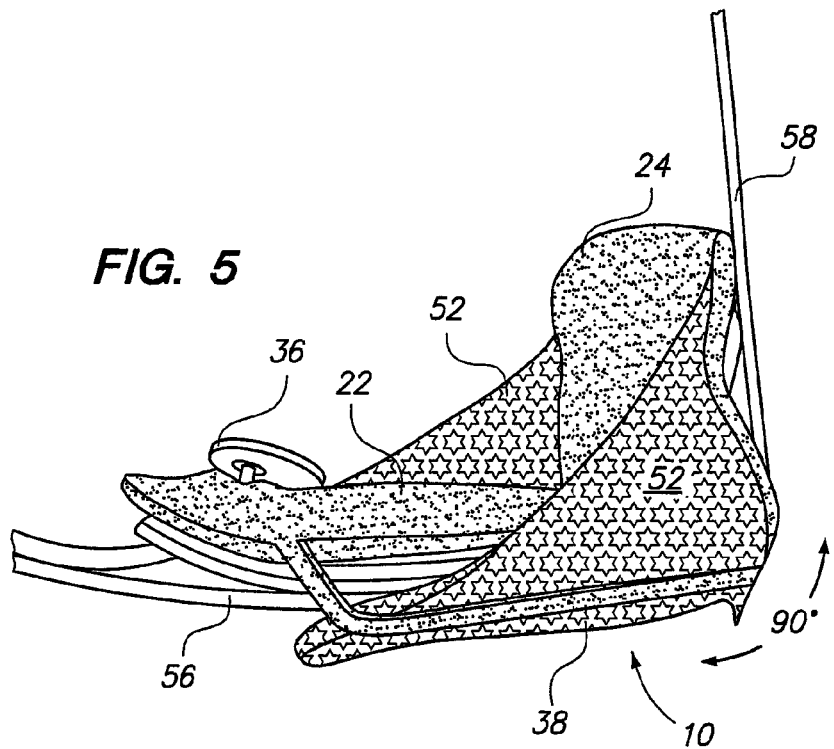
FIG. 5 is a plan perspective view of the inventive eyeglass patch attached to a pair of eyeglasses
Figure 6:
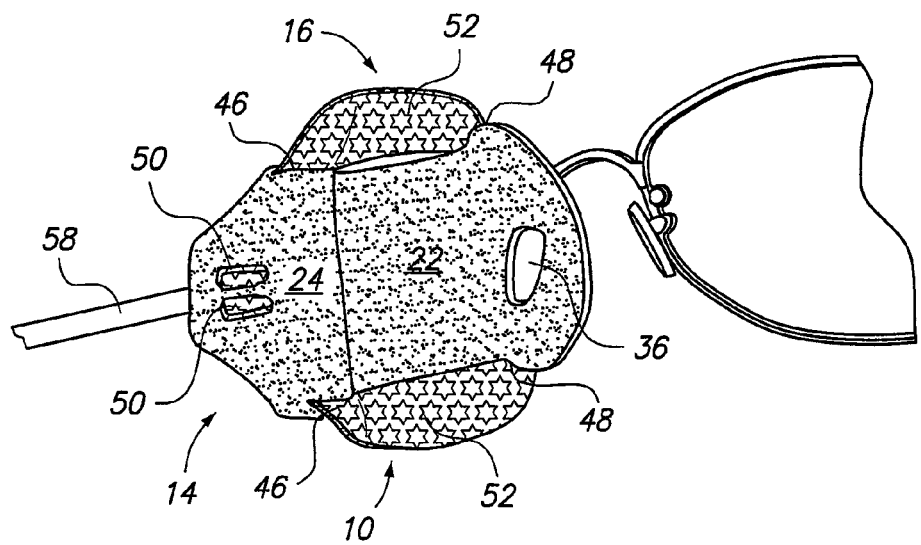
FIG. 6 is an elevated perspective view of the inventive eyeglass patch attached to a pair of eyeglasses, shown from the inside of a pair of eyeglasses.

FIGS. 3 and 4 illustrate the first and second cutouts 14, 16 respectively, prior to threading and interlocking the cutouts together, to create the present invention 10. First cutout 14 is a utilitarian eyeglass patch having a front shield 22 for blocking frontal vision and a side shield 24 for blocking peripheral vision. The front shield 22 is of a size necessary to cover the lens on standard eyeglass sizes, but larger or smaller eyeglass frames and lenses could be accommodated by sizing and forming the first and second cutouts as needed. The side shield 24 needs to be sized to block the wearer's peripheral vision from his dominant eye. The dotted line 26 shown in the Figures represents a line of demarcation separating the front and side shields; it is also where the front and side shields achieve an angled orientation in relation to each other, due to the second cutout 16 imparting a mechanical force to the first cutout 14, upon fully threading and interlocking the second cutout with the first cutout, as will be further described herein. First cutout 14 includes a plurality of through-slits 28, 30, 32 (28-32) for threading and interlocking with second cutout 16. Through-slits 28-32 are placed strategically to allow the mechanical force of the second cutout 16 to orient front and side shields 22, 24 into the angled orientation just mentioned. An additional through-slit 34 functions to attach the first cutout 14 over the bridge pad 36 of a pair of eyeglasses 12 as shown in FIGS. 5 and 6.

The first and second cutouts are preferably constructed from non-fraying materials or non-fraying laminates of materials. The materials, in addition to being non-fraying, should have a lens-friendly, scratch-free quality, at least on the sides of the cutouts which directly contact the eyeglass lenses. An example of a material which meets the requirements of the invention is a laminate of thin foam material sandwiched between two layers of Velvet Loop® material which is manufactured by Velcro Inc. The Velvet Loop® material in addition to being non-fraying and lens friendly is also durable enough to withstand frequent interchanges of the second cutout 16. Polyester double-knit or nylon materials also suffice as materials from which to construct first and second cutouts 14, 16. First and second cutouts 14, 16 are preferably die-cut for fast production, and due to their threading and interlocking design, eliminate time consuming sewing from the manufacturing process.

Figure 10:
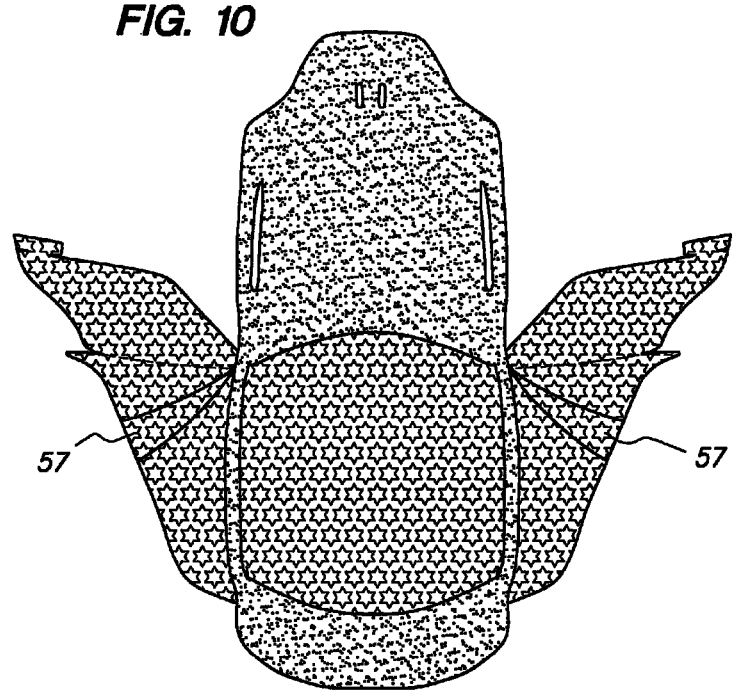
FIG. 10 illustrates an embodiment of the invention which is designed for a more relaxed fit for large wearers.

Still referring to the drawings, the second cutout 16 is comprised of an overlying member 38, which when completely in place, overlies the front shield 22 of the first cutout 14. Second cutout 16 is further comprised of threadable members 40, which flank the overlying member 38 and function to thread with the through-slits 28-32 of the first cutout 14. Dotted lines 42 represent boundaries separating the overlying member 38 from the threadable members 40. Threadable members 40 are endowed with locking points 44, 46, 48 (44-48), and locking tab 50 which lock sections 52, 54 of threadable members 40 in the through-slits 28-32 of first cutout 14. As each section 52, 54 of the threadable members 40 is locked in place within through-slits 28-32, the second 16 cutout imparts an increasingly mechanically shaping force upon the first cutout 14, ultimately orienting front and side shields 22, 24 of the first cutout 14 into an angled relation. The angled relation can approximate 90-degrees, which is approximate to the angle separating the temple 58 from the eyeglass frames 56. The approximate 90-degree relation as shown in FIG. 5 is closer to that needed by a smaller child who might not spread his eyeglass frames 56. However, in larger children, or even adults who have larger faces, the temple 58 and lens frames 56 might spread apart more, and the relation of the front 22 and side shield 24 should deviate further from 90-degrees to accommodate this spread; in such a case the mechanical force applied by the second cutout 16 would be less pronounced upon the first cutout 14, to achieve the more relaxed angled relation. This relaxed fit can be accomplished by adding more material at the location 57 shown in FIG. 10. Also, as further shown in FIGS. 5 and 6 the sections 52 of threadable elements 40 form upper and lower overlapping flaps, which overlap both the first cutout and the eyeglass frames. This overlapping by the second cutout 16 forms a "cup" around the wearer's dominant eye, which more effectively occludes the dominant eye.

Figure 7:
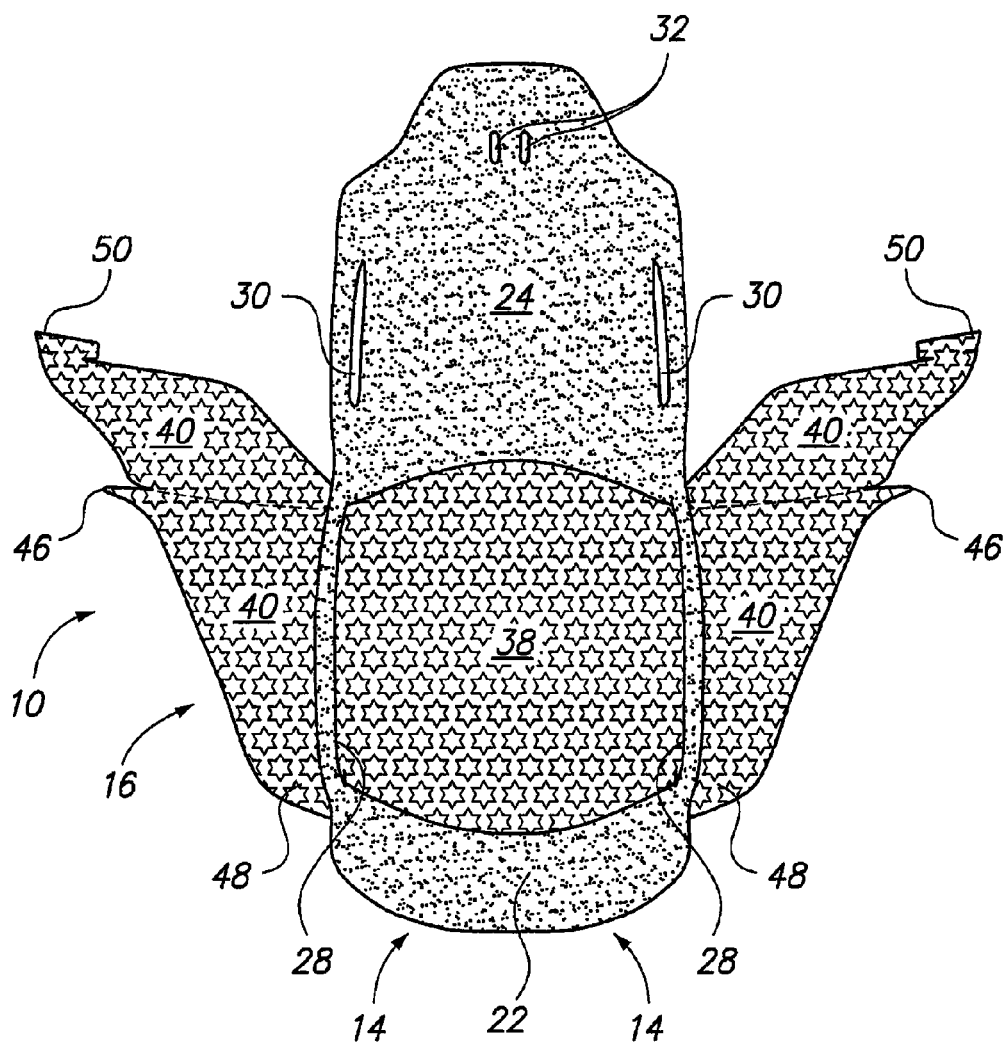
FIG. 7 illustrates a first step in threading and interlocking the second cutout into the first cutout in order to assemble the inventive eyeglass patch.
Figure 8:
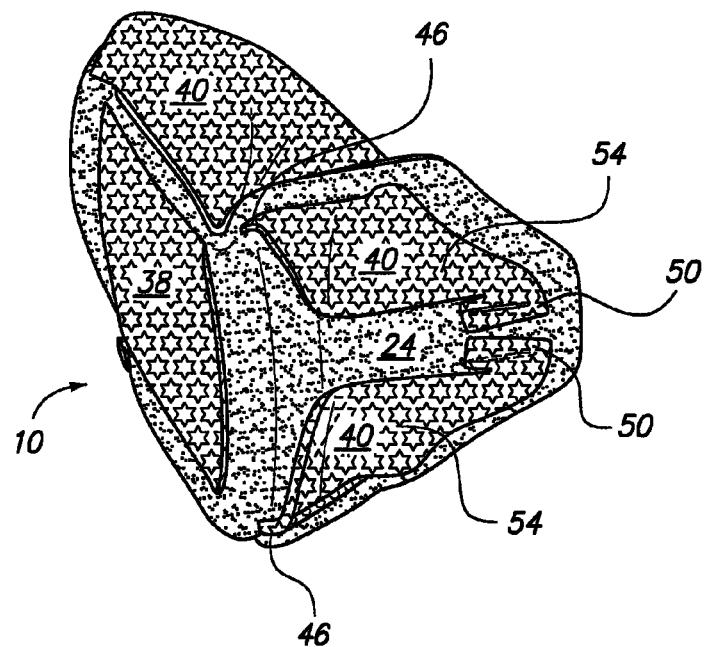
FIG. 8 illustrates a second step in threading and interlocking the second cutout into the first cutout in order to assemble the inventive eyeglass patch.
Figure 9:
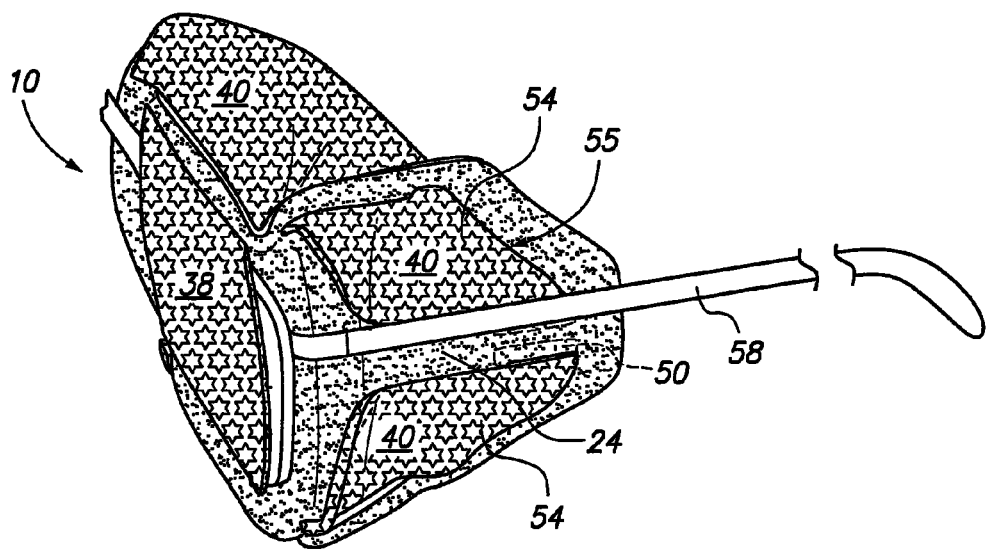
FIG. 9 illustrates a third step in threading and interlocking the second cutout into the first cutout in order to complete the assembly of the inventive eyeglass patch.

Referring now to FIGS. 7-9 the process of threading and interlocking second cutout 16 with first cutout 14 to form the inventive eyeglass patch 10 is shown. First, as shown in FIG. 7, threadable members 40 of second cutout are threaded through slits 28 located in the top and bottom of front shield 22 of first cutout 14, until locking points 44, 48 are forced through slits 28, thereby locking overlying member 38 over front shield 22. Next, as shown in FIG. 8, threadable members 40 are further threaded through top and bottom slits 30 of side shield 24, until locking points 46 engage with slits 30. The placement of locking points 44-48 at the locations shown on threadable members 40 forces the front and side shields 22, 24 of first cutout into the angled orientation previously noted. Next, as shown in FIG. 9 the end locking tabs 50 of threadable members 40 are threaded through the remaining slits 32 in side shield 24 to fully attach the second cutout 16 to the first cutout 14. The temple 58 of eyeglasses 12 can be threaded through the channel 55 formed between section 54 and side shield 24, for added stability, as shown. To remove the decorative second cutout 16, the wearer merely has to reverse the assembly process just described and shown in FIGS. 7-9, beginning with unlocking the locking tabs 50 of threadable members 40.

Figure 11:
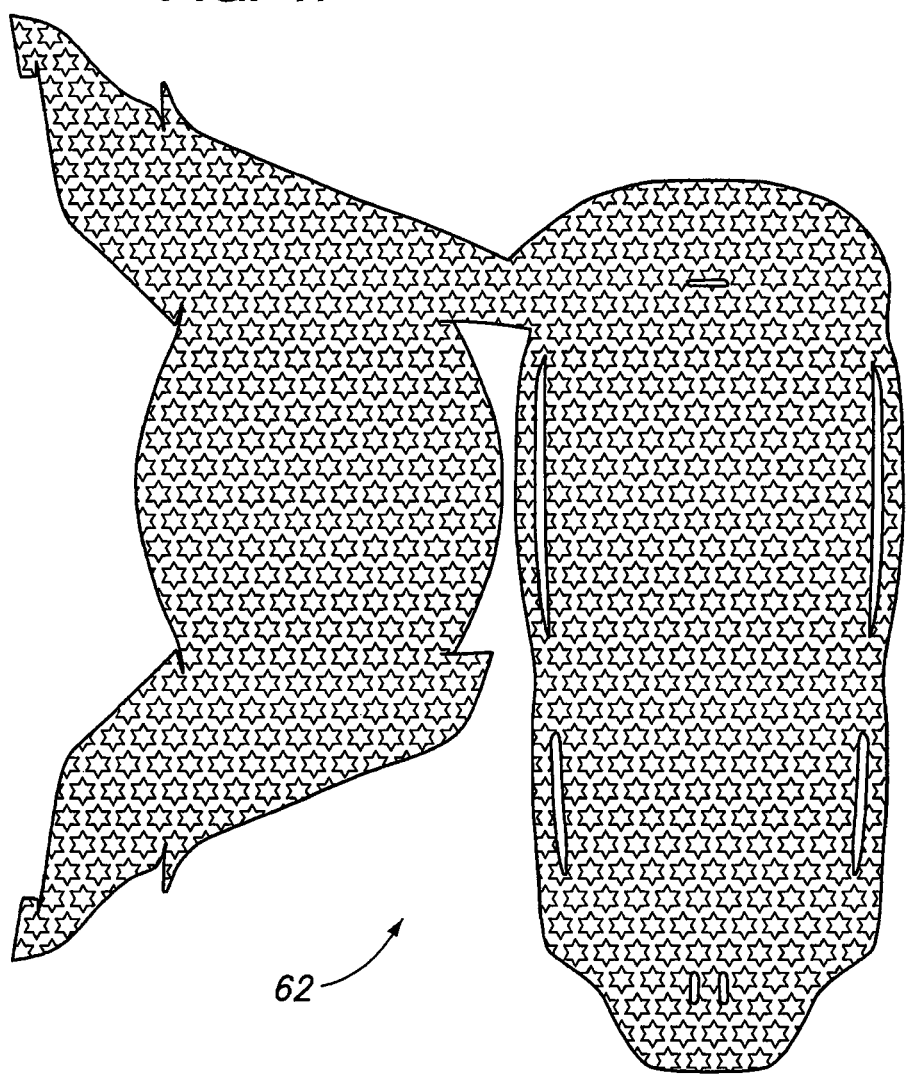
FIG. 11 illustrates an embodiment of the invention which is a one-piece die cut variant.

Also, while the previously described embodiment relies on two die cut pieces 14 and 16, it is possible for the invention to be reduced to a one-piece die cut embodiment 62 of the type shown in FIG. 11. This embodiment would form the occluding cup in the manner previously described for the two-piece version, however the decorative interchangeability as described herein would be lost.

The inventive corrective eyeglass patch allows a wearer to continually interchange second cutouts having a myriad of aesthetically pleasing designs. The present invention transforms the corrective eyeglass patch from an item of ridicule and derision to a fashion statement, wherein the wearer may express his individuality. It is hoped that the desirable decorative aspect of the present invention will especially encourage children to wear their corrective patches, thereby aiding in the strengthening and healing of their non-dominant eyes, as well as wear their eyeglass patches for any other medically necessary reason.

Finally, although the description above contains much specificity, these should not be construed as limiting the scope of the invention but as merely providing illustrations of some of the presently preferred embodiments of this invention. This invention may be altered and rearranged in numerous ways by one skilled in the art without departing from the coverage of any patent claims which are supported by this specification.

The invention claimed is:

1. An eyeglass patch comprising first and second interlocking cutouts, said cutouts further comprised of flexible material, said first cutout further comprising a front shield for blocking frontal vision and a side shield for blocking peripheral vision, said first cutout further comprising a plurality of through-slits, said second cutout further comprising an overlying member flanked by two threadable members, said second cutout further comprising a decorative exterior, said threadable members of said second cutout threading through said plurality of through-slits of said first cutout to interlock with said first cutout, wherein said threading and interlocking of said threadable members with said first cutout cause said overlying member of said second cutout to overlie said front shield of said first cutout and wherein said threading and interlocking of said threadable members with said first cutout further cause said threadable members to overlie said side shield.

2. The eye glass patch as recited in claim 1, wherein said threadable members thread and interlock with said first cutout to form flaps for overlapping above and below an eyeglass lens.

3. An eyeglass patch comprising first and second interlocking cutouts, said cutouts further comprised of flexible material, said first cutout further comprising a front shield for blocking frontal vision and a side shield for blocking peripheral vision, said first cutout further comprising a plurality of through-slits, said second cutout further comprising an overlying member flanked by two threadable members, said second cutout further comprising a decorative exterior, said threadable members threading through said plurality of through-slits to interlock with said first cutout, wherein said second cutout is comprised of a plurality of precisely located locking points, said locking points communicating and locking with said through-slits to form said front and side shields of said first cutout into an angled orientation.

4. The eyeglass patch as recited in claim 3, further comprising a through-channel located between said overlying member and said front shield, said through-channel for receiving a lens of a pair of eyeglasses there between.

* * * * *